(12) United States Patent
Alfieri (10) Patent No.: US 8,529,620 B2
(45) Date of Patent: Sep. 10, 2013

(54) INWARDLY-BOWED TRICUSPID ANNULOPLASTY RING

(76) Inventor: Ottavio Alfieri, Milan (IT)

( * ) Notice: Subject to any disclaimer, the term of this patent is extended or adjusted under 35 U.S.C. 154(b) by 512 days.

(21) Appl. No.: 12/111,454

(22) Filed: Apr. 29, 2008

(65) Prior Publication Data

US 2008/0275551 A1 Nov. 6, 2008

Related U.S. Application Data

(60) Provisional application No. 60/915,397, filed on May 1, 2007.

(51) Int. Cl.
*A61F 2/24* (2006.01)
(52) U.S. Cl.
USPC .......................... 623/2.36; 623/2.37
(58) Field of Classification Search
USPC ................. 623/2.1, 2.15, 1.24, 2.36–2.37
See application file for complete search history.

(56) References Cited

U.S. PATENT DOCUMENTS

| | | | |
|---|---|---|---|
| 3,656,185 A | 4/1972 | Carpentier | |
| 4,055,861 A | 11/1977 | Carpentier et al. | |
| 4,164,046 A | 8/1979 | Cooley | |
| 4,217,665 A | 8/1980 | Bex et al. | |
| 4,602,911 A | 7/1986 | Ahmadi et al. | |
| 5,041,130 A | 8/1991 | Cosgrove et al. | |
| 5,061,277 A | 10/1991 | Carpentier et al. | |
| 5,064,431 A | 11/1991 | Gilbertson et al. | |
| 5,104,407 A | 4/1992 | Lam et al. | |
| 5,201,880 A | 4/1993 | Wright et al. | |
| 5,258,021 A | 11/1993 | Duran | |
| 5,306,296 A | 4/1994 | Wright et al. | |
| 5,450,860 A | 9/1995 | O'Connor | |
| 5,496,336 A | 3/1996 | Cosgrove et al. | |
| 5,593,435 A | 1/1997 | Carpentier et al. | |
| 5,607,471 A | 3/1997 | Seguin et al. | |
| 5,674,279 A | 10/1997 | Wright et al. | |
| 5,716,397 A | 2/1998 | Myers | |
| 5,776,189 A | 7/1998 | Khalid | |
| 5,824,066 A | 10/1998 | Gross | |
| 5,888,240 A | 3/1999 | Carpentier et al. | |
| 5,957,977 A | 9/1999 | Melvin | |
| 5,972,030 A | 10/1999 | Garrison et al. | |

(Continued)

FOREIGN PATENT DOCUMENTS

| | | |
|---|---|---|
| EP | 0338994 A1 | 10/1989 |
| EP | 1034753 A1 | 9/2000 |

(Continued)

OTHER PUBLICATIONS

PCT International Search Report for Application No. PCT/US2008/082018, dated Jul. 22, 2008.

(Continued)

*Primary Examiner* — Thomas J Sweet
*Assistant Examiner* — Seema Mathew
(74) *Attorney, Agent, or Firm* — AnneMarie Kaiser; Guy Cumberbatch (57) ABSTRACT

A prosthetic tricuspid remodeling annuloplasty ring having two free ends and at least one inward bow to help reduce chordal tethering. The ring may have segments corresponding to the anterior, posterior and septal leaflets, with inward bows located adjacent one, two or all leaflets. Convex corners separate the concave inward bows, with inflection points therebetween. The ring has a semi-rigid inner body covered by fabric or a suture interface such as silicone and fabric.

21 Claims, 5 Drawing Sheets

(56) References Cited

U.S. PATENT DOCUMENTS

| | | |
|---|---|---|
| 6,074,417 A | 6/2000 | Peredo |
| 6,102,945 A | 8/2000 | Campbell |
| 6,143,024 A | 11/2000 | Campbell et al. |
| 6,159,240 A | 12/2000 | Sparer et al. |
| 6,183,512 B1 | 2/2001 | Howanec, Jr. et al. |
| 6,187,040 B1 | 2/2001 | Wright |
| 6,217,610 B1 * | 4/2001 | Carpentier et al. ........... 623/2.37 |
| 6,231,602 B1 | 5/2001 | Carpentier et al. |
| 6,250,308 B1 | 6/2001 | Cox |
| 6,258,122 B1 | 7/2001 | Tweden et al. |
| 6,332,893 B1 | 12/2001 | Mortier et al. |
| 6,368,348 B1 | 4/2002 | Gabbay |
| 6,391,054 B2 * | 5/2002 | Carpentier et al. ........... 623/2.37 |
| 6,406,493 B1 | 6/2002 | Tu et al. |
| 6,416,548 B2 | 7/2002 | Chinn et al. |
| 6,419,696 B1 | 7/2002 | Ortiz et al. |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,629,534 B1 | 10/2003 | St. Goar et al. |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,764,510 B2 | 7/2004 | Vidlund et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,858,039 B2 | 2/2005 | McCarthy |
| 6,908,482 B2 * | 6/2005 | McCarthy et al. ........... 623/2.36 |
| 6,918,917 B1 | 7/2005 | Nguyen et al. |
| 6,921,407 B2 | 7/2005 | Nguyen et al. |
| 6,942,694 B2 | 9/2005 | Liddicoat et al. |
| 6,955,689 B2 | 10/2005 | Ryan et al. |
| 6,966,924 B2 | 11/2005 | Holmberg |
| 6,986,775 B2 | 1/2006 | Morales et al. |
| 6,997,950 B2 | 2/2006 | Chawla |
| 7,087,079 B2 | 8/2006 | Navia et al. |
| 7,101,395 B2 | 9/2006 | Tremulis et al. |
| 7,118,595 B2 | 10/2006 | Ryan et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,189,258 B2 | 3/2007 | Johnson et al. |
| 7,294,148 B2 | 11/2007 | McCarthy |
| 7,329,280 B2 * | 2/2008 | Bolling et al. ........... 623/2.36 |
| 7,361,190 B2 | 4/2008 | Shaoulian et al. |
| 7,367,991 B2 | 5/2008 | McCarthy et al. |
| 7,371,259 B2 | 5/2008 | Ryan et al. |
| 7,452,376 B2 | 11/2008 | Lim et al. |
| 7,608,103 B2 | 10/2009 | McCarthy |
| 7,642,684 B2 | 1/2010 | Himmelmann et al. |
| 7,879,087 B2 | 2/2011 | Roberts |
| 7,927,370 B2 | 4/2011 | Webler et al. |
| 7,942,928 B2 | 5/2011 | Webler et al. |
| 7,959,673 B2 | 6/2011 | Carpentier et al. |
| 7,993,395 B2 | 8/2011 | Vanermen et al. |
| 8,016,882 B2 * | 9/2011 | Macoviak et al. ........... 623/2.36 |
| 8,142,494 B2 * | 3/2012 | Rahdert et al. ........... 623/2.36 |
| 2001/0010018 A1 | 7/2001 | Cosgrove et al. |
| 2001/0021874 A1 | 9/2001 | Carpentier et al. |
| 2001/0049557 A1 | 12/2001 | Chinn et al. |
| 2002/0133180 A1 | 9/2002 | Ryan et al. |
| 2003/0033009 A1 | 2/2003 | Gabbay |
| 2003/0040793 A1 | 2/2003 | Marquez |
| 2003/0045929 A1 | 3/2003 | McCarthy et al. |
| 2003/0050693 A1 | 3/2003 | Quijano et al. |
| 2003/0083742 A1 | 5/2003 | Spence et al. |
| 2003/0093148 A1 * | 5/2003 | Bolling et al. ........... 623/2.36 |
| 2003/0176917 A1 | 9/2003 | Ryan et al. |
| 2003/0199975 A1 | 10/2003 | Gabbay |
| 2004/0127982 A1 * | 7/2004 | Machold et al. ........... 623/2.36 |
| 2004/0249452 A1 | 12/2004 | Adams et al. |
| 2004/0249453 A1 | 12/2004 | Cartledge et al. |
| 2004/0260393 A1 * | 12/2004 | Rahdert et al. ........... 623/2.36 |
| 2005/0004665 A1 | 1/2005 | Aklog |
| 2005/0004669 A1 | 1/2005 | Sievers |
| 2005/0038509 A1 | 2/2005 | Ashe |
| 2005/0043791 A1 | 2/2005 | McCarthy et al. |
| 2005/0131533 A1 * | 6/2005 | Alfieri et al. ........... 623/2.36 |
| 2005/0182487 A1 | 8/2005 | McCarthy et al. |
| 2005/0192666 A1 | 9/2005 | McCarthy |
| 2005/0256567 A1 | 11/2005 | Lim et al. |
| 2005/0256568 A1 | 11/2005 | Lim et al. |
| 2005/0267572 A1 | 12/2005 | Schoon et al. |
| 2005/0278022 A1 | 12/2005 | Lim |
| 2005/0288781 A1 | 12/2005 | Moaddeb et al. |
| 2006/0015178 A1 | 1/2006 | Moaddeb et al. |
| 2006/0015179 A1 | 1/2006 | Bulman-Fleming et al. |
| 2006/0020336 A1 | 1/2006 | Liddicoat |
| 2006/0025858 A1 | 2/2006 | Alameddine |
| 2006/0030885 A1 | 2/2006 | Hyde |
| 2006/0069430 A9 * | 3/2006 | Rahdert et al. ........... 623/2.36 |
| 2006/0100697 A1 * | 5/2006 | Casanova ........... 623/2.11 |
| 2006/0129236 A1 * | 6/2006 | McCarthy ........... 623/2.36 |
| 2006/0184241 A1 | 8/2006 | Marquez |
| 2006/0217803 A1 * | 9/2006 | Ingle et al. ........... 623/2.11 |
| 2006/0229708 A1 | 10/2006 | Powell et al. |
| 2007/0038296 A1 | 2/2007 | Navia et al. |
| 2007/0050022 A1 * | 3/2007 | Vidlund et al. ........... 623/2.37 |
| 2007/0100441 A1 | 5/2007 | Kron et al. |
| 2007/0156234 A1 * | 7/2007 | Adzich et al. ........... 623/2.11 |
| 2007/0162111 A1 | 7/2007 | Fukamachi et al. |
| 2007/0162112 A1 | 7/2007 | Burriesci et al. |
| 2007/0173931 A1 | 7/2007 | Tremulis et al. |
| 2007/0191940 A1 | 8/2007 | Arru et al. |
| 2007/0299513 A1 | 12/2007 | Ryan et al. |
| 2008/0058924 A1 * | 3/2008 | Ingle et al. ........... 623/2.36 |
| 2008/0086203 A1 | 4/2008 | Roberts |
| 2008/0091059 A1 | 4/2008 | Machold et al. |
| 2009/0036979 A1 * | 2/2009 | Redmond et al. ........... 623/2.36 |
| 2009/0132036 A1 | 5/2009 | Navia |
| 2009/0157176 A1 | 6/2009 | Carpentier et al. |
| 2009/0177276 A1 | 7/2009 | Carpentier et al. |
| 2009/0177278 A1 | 7/2009 | Spence |
| 2009/0192602 A1 | 7/2009 | Kuehn |
| 2009/0192603 A1 | 7/2009 | Ryan |
| 2009/0192604 A1 | 7/2009 | Gloss |
| 2009/0192606 A1 | 7/2009 | Gloss et al. |
| 2009/0264996 A1 | 10/2009 | Vanermen et al. |
| 2009/0276038 A1 | 11/2009 | Tremulis et al. |
| 2009/0287303 A1 * | 11/2009 | Carpentier ........... 623/2.36 |
| 2010/0076549 A1 | 3/2010 | Keidar et al. |
| 2010/0076551 A1 | 3/2010 | Drake |
| 2010/0145440 A1 | 6/2010 | Keranen |
| 2010/0152844 A1 | 6/2010 | Couetil |
| 2010/0168845 A1 | 7/2010 | Wright |
| 2010/0174365 A1 | 7/2010 | Parravicini et al. |
| 2011/0160849 A1 * | 6/2011 | Carpentier et al. ........... 623/2.19 |
| 2012/0071970 A1 * | 3/2012 | Carpentier et al. ........... 623/2.37 |

FOREIGN PATENT DOCUMENTS

| | | |
|---|---|---|
| EP | 1629795 | 3/2006 |
| WO | 03034950 A1 | 5/2003 |
| WO | WO 2005/034813 | 4/2005 |
| WO | WO 2005/112830 | 12/2005 |

OTHER PUBLICATIONS

Adams, David, et al., "Large Annuloplasty Rings Facilitate Mitral Valve Repair in Barlow's Disease," Society of Thoracic Surgeons 42nd Annual Meeting, Jan. 30-Feb. 1, 2006.

Alonso-Lei, M.D., et al., Adjustable Annuloplasty for Tricuspid Insufficiency, The annals of Thoracic Surgery, vol. 46, No. 3, pp. 368-369, Sep. 1988.

Bolling, Mitral Valve Reconstruction in the Patient With Heart Failure, Heart Failure Reviews, 6, pp. 177-185, 2001.

Bolling, et al., Surgical Alternatives for Heart Failure, The Journal of Heart and Lung Transplantation, vol. 20, No. 7, pp. 729-733, 2001.

Carpentier, et al. "The 'Physio-Ring': An Advanced Concept in Mitral Valve Annuloplasty," Society of Thoracic Surgeons 31st Annual meeting, Jan. 30-Feb. 2, 1995.

Carpentier-Edwards Classic Annuloplasty Ring With Duraflo Treatment Models 4425 and 4525 for Mitral and Tricuspid Valvuloplsty, Baxter Healthcare Corporation, 1998.

Carpentier-Edwards Pyshio Annuloplasty Ring, Edwards Lifesciences Corporation, 2003.

Carpentier, et al., Reconstructive Valve Surgery, Chapter 19—Reconstructive Techniques, ISBN No. 978-0-7216-9168-8, Sanders Elsevier Publishing, Maryland Heights, Missouri, 2010.

Flachskampf, Frank A., et al. "Analysis of Shape and Motion of the Mitral Annulus in Subjects With and Without Cardiomyopathy by Echocardiographic 3-Dimensional Reconstruction," American Society of Echocardiography 0894-7317/2000.

Gatti, et al., Preliminary Experience in Mitral Valve Repair Using the Cosgrove-Edwards Annuloplasty Ring, Interactive Cardiovascular and Thoracic Surgery, vol. 2(3), pp. 256-261, 2003.

Melo, et al., Atrioventricular Valve Repair Using Externally Adjustable Flexible Rings: The Journal of Thoracic Cardiovascular Surgery, vol. 110, No. 5, 1995.

MGH Study Shows Mitral Valve Prolapse Not a Stroke Risk Factor, Massachusetts General Hospital, pp. 1-3, Jun. 1999.

Miller, D. Craig, M.D., "Ischemic Mitral Regurgitation Redux—To Repair or Replace?", The Journal of Thoracic & Cardiovascular Surgery, Dec. 2001, vol. 122, No. 6, pp. 1059-1062.

Salgo, et al., Effect of Annular Shape on Leaflet Curvature in Reducing Mitral Leaflet, American Heart Association, Circulation 200; pp. 106-711.

Seguin, et al., Advance in Mitral Valve Repair Using a Device Flexible in Three Dimensions, The St. Jude Medical Seguin Annuloplasty Ring, ASAIO Journal, vol. 42, No. 6, pp. 368-371, 1996.

Smolens, et al., Mitral Valve Repair in Heart Failure, The European Journal of Heart Failure 2, pp. 365-371, 2000.

Watanabe, Nozomi, et al. "Mitral Annulus Flattens in Ischemic Mitral Regurgitation: Geometric Differences Between Inferior and Anterior Myocardial Infarction: A Real-Time 3-Dimensional Echocardiographic Study," American Heart Association © 2005; ISSN: 1524-4539.

* cited by examiner

INWARDLY-BOWED TRICUSPID ANNULOPLASTY RING

RELATED APPLICATIONS

The present invention claims priority under 35 U.S.C. §119(e) to Provisional Application No. 60/915,397, filed on May 1, 2007.

FIELD OF THE INVENTION

The present invention relates generally to medical devices and particularly to a tricuspid annuloplasty ring having inward bows around its periphery.

BACKGROUND OF THE INVENTION

For the purposes of anatomic orientation, when the body is viewed in the upright position it has 3 orthogonal axes: superior-inferior (up-down), posterior-anterior (back-front), and right-left.

Figure 1:
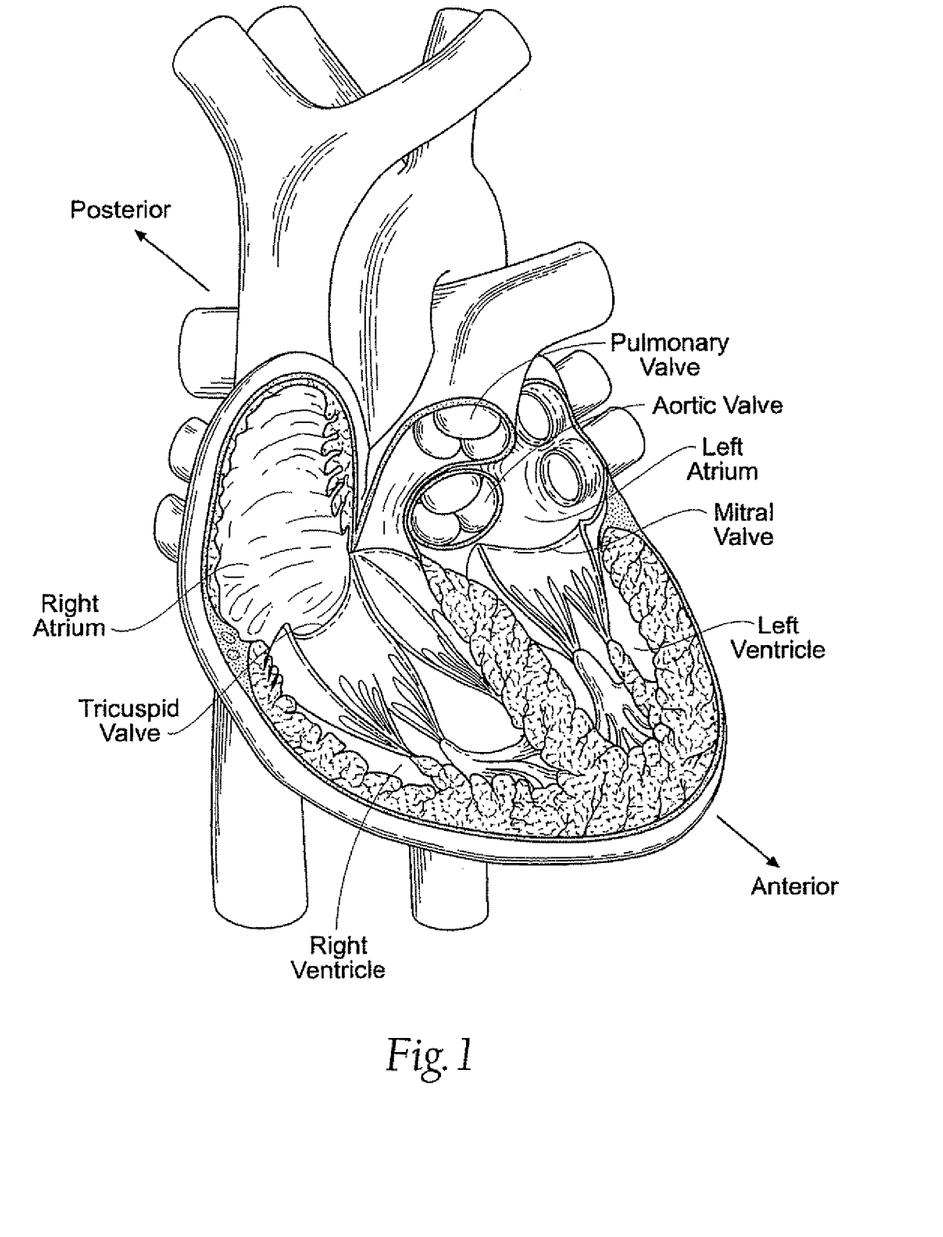
FIG. 1 is an anatomic anterior view of a human heart, with portions broken away and in section to view the interior heart chambers and adjacent structures.

In vertebrate animals, the heart is a hollow muscular organ having four pumping chambers as seen in FIG. 1: the left and right atria and the left and right ventricles, each provided with its own one-way valve. The natural heart valves are identified as the aortic, mitral (or bicuspid), tricuspid and pulmonary, and are each mounted in an annulus comprising dense fibrous rings attached either directly or indirectly to the atrial and ventricular muscle fibers. Each annulus defines a flow orifice. The tricuspid and mitral valves together define the atrioventricular (AV) junctions.

The atriums are the blood-receiving chambers, which pump blood into the ventricles. The ventricles are the blood-discharging chambers. A wall composed of fibrous and muscular parts, called the interatrial septum separates the right and left atriums (see FIGS. 2 to 4). The fibrous interatrial septum is a materially stronger tissue structure compared to the more friable muscle tissue of the heart. An anatomic landmark on the interatrial septum is an oval, thumbprint sized depression called the oval fossa, or fossa ovalis (shown in FIG. 4).

The synchronous pumping actions of the left and right sides of the heart constitute the cardiac cycle. The cycle begins with a period of ventricular relaxation, called ventricular diastole. The cycle ends with a period of ventricular contraction, called ventricular systole. The four valves (see FIGS. 2 and 3) ensure that blood does not flow in the wrong direction during the cardiac cycle; that is, to ensure that the blood does not back flow from the ventricles into the corresponding atria, or back flow from the arteries into the corresponding ventricles. The mitral valve is between the left atrium and the left ventricle, the tricuspid valve between the right atrium and the right ventricle, the pulmonary valve is at the opening of the pulmonary artery, and the aortic valve is at the opening of the aorta.

Figures 2, 3, 4:
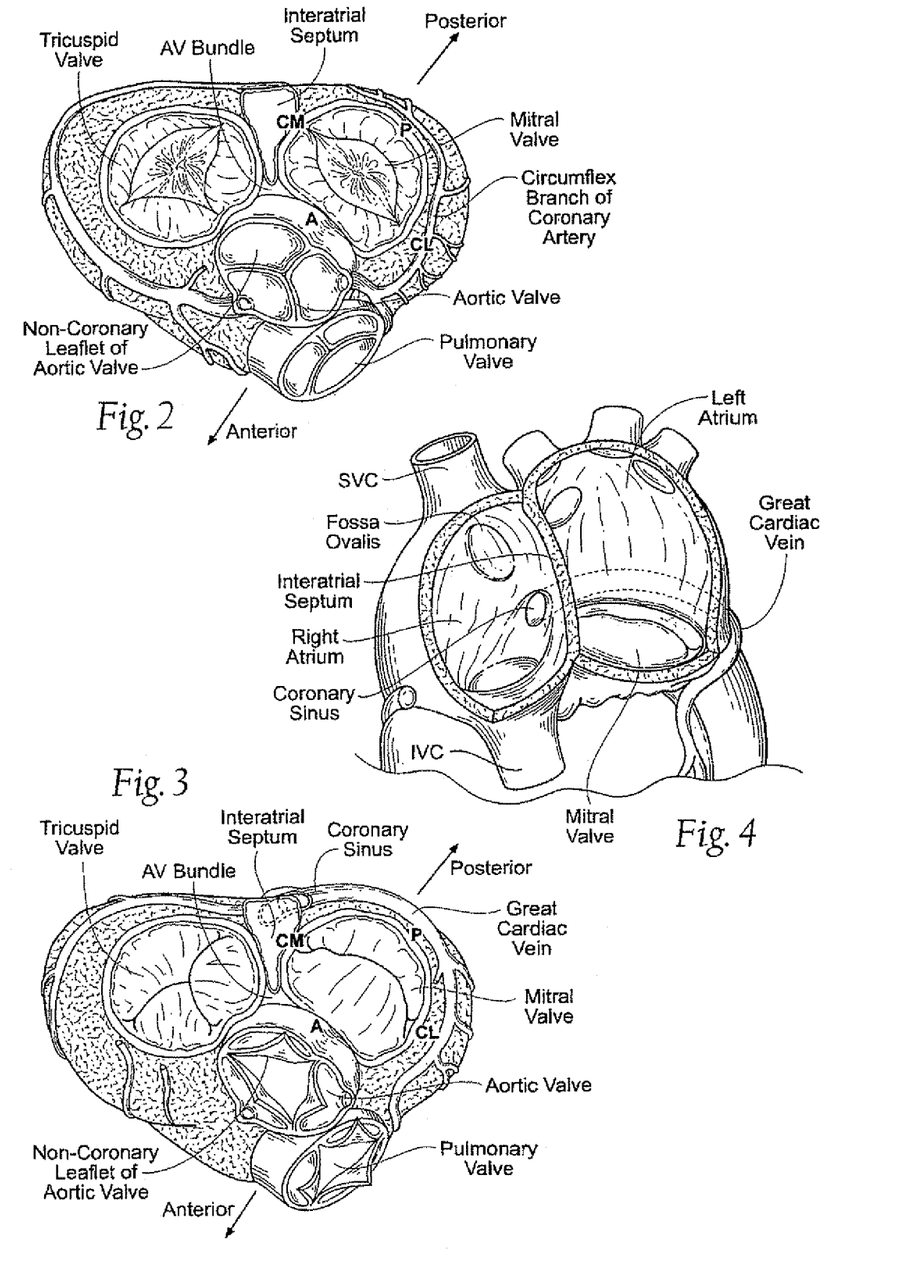
FIG. 2 is an anatomic superior view of a section of the human heart showing the tricuspid valve in the right atrium, the mitral valve in the left atrium, and the aortic valve in between, with the tricuspid and mitral valves open and the aortic and pulmonary valves closed during ventricular diastole (ventricular filling) of the cardiac cycle.
FIG. 3 is an anatomic superior view of a section of the human heart shown in FIG. 2, with the tricuspid and mitral valves closed and the aortic and pulmonary valves opened during ventricular systole (ventricular emptying) of the cardiac cycle.
FIG. 4 is an anatomic anterior perspective view of the left and right atriums, with portions broken away and in section to show the interior of the heart chambers and associated structures, such as the fossa ovalis, coronary sinus, and the great cardiac vein.

FIGS. 2 and 3 show the anterior (A) portion of the mitral valve annulus abutting the non-coronary leaflet of the aortic valve. The mitral valve annulus is in the vicinity of the circumflex branch of the left coronary artery, and the posterior (P) side is near the coronary sinus and its tributaries.

The mitral and tricuspid valves are defined by fibrous rings of collagen, each called an annulus, which forms a part of the fibrous skeleton of the heart. The annulus provides peripheral attachments for the two cusps or leaflets of the mitral valve (called the anterior and posterior cusps) and the three cusps or leaflets of the tricuspid valve. The free edges of the leaflets connect to chordae tendineae from more than one papillary muscle, as seen in FIG. 1. In a healthy heart, these muscles and their tendinous chords support the mitral and tricuspid valves, allowing the leaflets to resist the high pressure developed during contractions (pumping) of the left and right ventricles.

When the left ventricle contracts after filling with blood from the left atrium, the walls of the ventricle move inward and release some of the tension from the papillary muscle and chords. The blood pushed up against the undersurface of the mitral leaflets causes them to rise toward the annulus plane of the mitral valve. As they progress toward the annulus, the leading edges of the anterior and posterior leaflet come together forming a seal and closing the valve. In the healthy heart, leaflet coaptation occurs near the plane of the mitral annulus. The blood continues to be pressurized in the left ventricle until it is ejected into the aorta. Contraction of the papillary muscles is simultaneous with the contraction of the ventricle and serves to keep healthy valve leaflets tightly shut at peak contraction pressures exerted by the ventricle.

In a like manner, the tricuspid valve controls the backflow of blood from the right ventricle into the right atrium during contraction of the right ventricle. Contraction of the right ventricle occurs simultaneously with contraction of the papillary muscles, keeping the healthy tricuspid valve leaflets shut at peak ventricular contraction pressures. Tricuspid regurgitation involves backward flow of blood across the tricuspid valve into the right atrium. The most common cause of tricuspid regurgitation is not damage to the valve itself but enlargement of the right ventricle, which may be a complication of any disorder that causes failure of the right ventricle. Other diseases can directly affect the tricuspid valve. The most common of these is rheumatic fever, which is a complication of untreated strep throat infections. The valve fails to close properly, and blood can flow back to the right atrium from the right ventricle, and from there back into the veins. This reduces the flow of blood forward into the lungs.

Various surgical techniques may be used to repair a diseased or damaged valve. In a valve replacement operation, the damaged leaflets are excised and the annulus sculpted to receive a replacement valve. Another less drastic method for treating defective valves is through repair or reconstruction, which is typically used on minimally calcified valves. By interrupting the cycle of progressive functional mitral regurgitation, studies have shown increased survival and even increased forward ejection fraction in many surgical patients. The problem with surgical therapy is the significant insult it imposes on these chronically ill patients with high morbidity and mortality rates associated with surgical repair.

Surgical edge-to-edge juncture repairs, which can be performed endovascularly, are also made, in which a mid-valve leaflet to mid-valve leaflet suture or clip is applied to keep these points of the leaflet held together throughout the cardiac cycle. Other efforts have developed an endovascular suture and a clip to grasp and bond the two mitral leaflets in the beating heart. Grade 3+ or 4+ organic mitral regurgitation may be repaired with such edge-to-edge technologies. This is because, in organic mitral regurgitation, the problem is not the annulus but in the central valve components. However, functional mitral regurgitation can persist at a high level, even after edge-to-edge repair, particularly in cases of high Grade 3+ and 4+ functional mitral regurgitation. After surgery, the repaired valve may progress to high rates of functional mitral regurgitation over time.

In yet another emerging technology, the coronary sinus is mechanically deformed through endovascular means applied and contained to function solely within the coronary sinus.

One repair technique that has been shown to be effective ill treating incompetence is annuloplasty, or reconstruction of the ring (or annulus) of an incompetent cardiac valve. The repair may be done entirely surgically, by cutting out a segment of leaflet and re-attaching the cut sides with sutures. However, more typically the annulus is reshaped by attaching a prosthetic annuloplasty repair segment or ring thereto. For instance, the goal of a posterior mitral annulus repair is to bring the posterior mitral leaflet forward toward to the anterior leaflet to better allow coaptation. The annuloplasty ring is designed to support the functional changes that occur during the cardiac cycle: maintaining coaptation and valve integrity to prevent reverse flow while permitting good hemodynamics during forward flow.

The annuloplasty ring typically comprises an inner substrate or core of a metal such as a rod or multiple bands of stainless steel or titanium, or a flexible material such as silicone rubber or Dacron cordage, covered with a biocompatible fabric or cloth to allow the ring to be sutured to the fibrous annulus tissue. More rigid cores are typically surrounded by an outer cover of both silicone and fabric as a suture-permeable anchoring margin. Annuloplasty rings may be stiff or flexible, split or continuous, and may have a variety of shapes in plan view, including circular, D-shaped, C-shaped, or kidney-shaped. Examples are seen in U.S. Pat. Nos. 5,041,130, 5,104,407, 5,201,880, 5,258,021, 5,607,471 and, 6,187,040. In the context of the present invention, the term annuloplasty ring encompasses rings both open (e.g., C-shaped) and closed (e.g., D-shaped), as well as shorter segments, bands, or other such terms for a prosthesis that at least partly encircles and attaches to an annulus to reshape or correct a dysfunction in the annulus.

Most rigid and semi-rigid annular rings for the mitral valve have a kidney-like or D shape, with a relatively straight anterior segment co-extensive with the anterior valve leaflet, and a curved posterior segment co-extensive with the posterior valve leaflet. The shape of the annular rings reproduces the configuration of the valve annulus during the ventricular systole, and therefore in the stage of the valve closing. The ratio between minor axis and major axis is typically 3:4 in most models currently on the market since it reproduces normal anatomical ratios. Most of the earlier mitral rings were planar, while some (e.g., U.S. Pat. Nos. 5,104,407, 5,201,880, and 5,607,471) are bowed upward on their anterior segment (and slightly on their posterior segment) to accommodate the three-dimensional saddle shape of the anterior aspect of the mitral annulus. Newer rings have larger posterior bows (e.g., U.S. Pat. Nos. 6,805,710 and 6,858,039), or other three-dimensional configurations.

Tricuspid rings are sold in various configurations. For example, the Carpentier-Edwards Classic® Tricuspid Annuloplasty Ring sold by Edwards Lifesciences Corporation of Irvine, Calif., is a C-shaped ring with an inner titanium core covered by a layer of silicone and fabric. Rings for sizes 26 mm through 36 mm in 2 mm increments have outside diameters (OD) between 31.2-41.2 mm, and inside diameters (ID) between 24.3-34.3 mm. These diameters are taken along the "diametric" line spanning the greatest length across the ring because that is the conventional sizing parameter.

Correction of the aortic annulus requires a much different ring than for a mitral annulus. For example, U.S. Pat. Nos. 5,258,021 and 6,231,602 disclose sinusoidal or so-called "scalloped" annuloplasty rings that follow the up-and-down shape of the three cusp aortic annulus. Such rings would not be suitable for correcting a mitral valve deficiency.

In the usual annuloplasty ring implant procedure, an array of separate implant sutures are first looped through all or portions of the exposed annulus at intervals spaced equidistant from one another, such as for example 4 mm intervals. The surgeon then threads the implant sutures through the annuloplasty ring at more closely spaced intervals, such as for example 2 mm. This occurs with the prosthesis outside the body, typically secured to a peripheral edge of a holder or template. Despite the advantage of increases visibility, instances of snagging of the inner core with the implant sutures have occurred.

The ring on the holder is then advanced (parachuted) distally along the array of pre-anchored implant sutures into contact with the valve annulus, thus effecting a reduction in valve annulus circumference. At this point a handle used to manipulate the holder or template is typically detached for greater visibility of the surgical field. The surgeon ties off the implant sutures on the proximal side of the ring, and releases the ring from the holder or template, typically by severing connecting sutures at a series of cutting guides. Although sutures are typically used, other flexible filaments to connect the ring to the holder may be suitable. Because of the presence of multiple implant and connecting sutures in the surgical fields, the step of disconnecting the ring from the holder with a scalpel is somewhat delicate, and can be confusing for the novice. It should be noted that a similar holder connection and implant procedure, with attendant drawbacks, are also common for implanting prosthetic valves.

The present application has particular relevance to the repair of the tricuspid valve, which regulates blood flow between the right atrium and right ventricle, although certain aspects may apply to repair of other of the heart valves.

Four structures embedded in the wall of the heart conduct impulses through the cardiac muscle to cause first the atria then the ventricles to contract. These structures are the sinoatrial node (SA node), the atrioventricular node (AV n-ode), the bundle of His, and the Purkinje fibers. On the rear wall of the right atrium is a barely visible knot of tissue known as the sinoatrial, or SA node. This tiny area is the control of the heart's pacemaker mechanism. Impulse conduction normally starts in the SA node. It generates a brief electrical impulse of low intensity approximately 72 times every minute in a resting adult. From this point the impulse spreads out over the sheets of tissue that make up the two atria, exciting the muscle fibers as it does so. This causes contraction of the two atria and thereby thrusts the blood into the empty ventricles. The impulse quickly reaches another small specialized knot of tissue known as the atrioventricular, or AV node, located between the atria and the ventricles. This node delays the impulse for about 0.07 seconds, which is exactly enough time to allow the atria to complete their contractions. When the impulses reach the AV node, they are relayed by way of the several bundles of His and Purkinje fibers to the ventricles, causing them to contract. As those of skill in the art are aware, the integrity and proper functioning of the conductive system of the heart is critical for good health.

Figure 5:
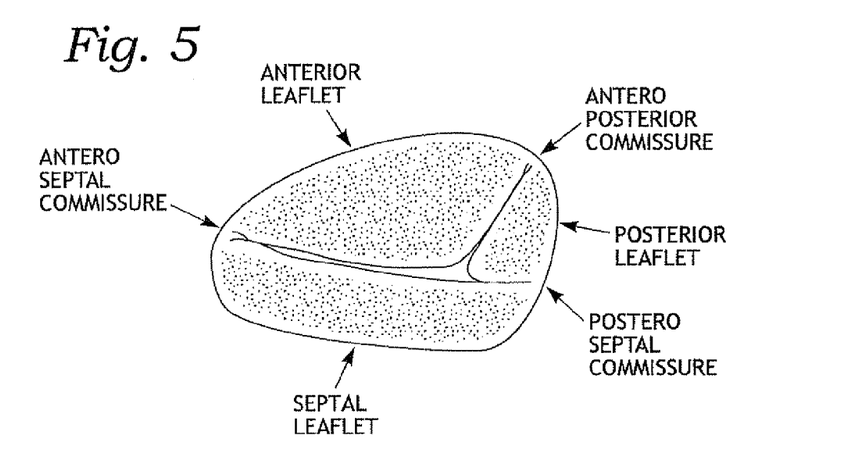
FIG. 5 is a schematic plan view of the tricuspid annulus with typical orientation directions noted as seen from the inflow side.

FIG. 5 is a schematic view of the tricuspid valve orifice seen from its inflow side (from the right atrium), with the peripheral landmarks labeled as: antero septal commissure, anterior leaflet, posterior commissure, antero posterior leaflet, postero septal commissure, and septal leaflet. Contrary to traditional orientation nomenclature, the tricuspid valve is nearly vertical, as reflected by these sector markings.

Figure 6:
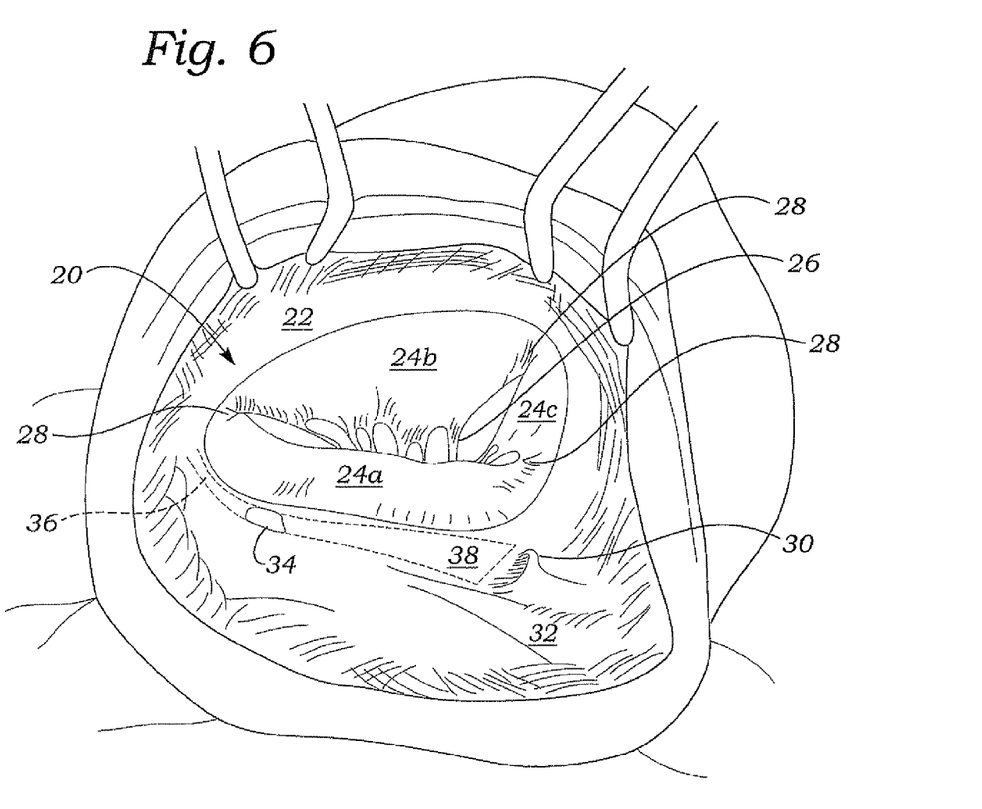
FIG. 6 is a plan view of the native tricuspid valve and surrounding anatomy from the inflow side.

From the same viewpoint, the tricuspid valve 20 is shown surgically exposed in FIG. 6 with an annulus 22 and three leaflets 24a, 24b, 24c extending inward into the flow orifice. Chordae tendineae 26 connect the leaflets to papillary muscles located in the RV to control the movement of the leaflets. The tricuspid annulus 22 is an ovoid-shaped fibrous ring at the base of the valve that is less prominent than the mitral annulus, but larger in circumference.

Reflecting their true anatomic location, the three leaflets in FIG. 6 are identified as septal 24a, anterior 24b, and posterior (or mural) 24c. The leaflets join together over three prominent zones of apposition, and the peripheral intersections of these zones are usually described as commissures 28, separately identified above. The leaflets 24 are tethered at the commissures 28 by the fan-shaped chordae tendineae 26 arising from prominent papillary muscles originating in the right ventricle. That portion of the annulus 22 at the base of the septal leaflet 24a is the site of attachment to the fibrous trigone, the fibrous "skeletal" structure within the heart. The anterior leaflet 24b, largest of the 3 leaflets, often has notches. The posterior leaflet 24c, smallest of the 3 leaflets, usually is scalloped.

The ostium 30 of the right coronary sinus opens into the right atrium, and the tendon of Todaro 32 extends adjacent thereto. The AV node 34 and the beginning of the bundle of His 36 are located in the supero-septal region of the tricuspid valve circumference. The AV node 34 is situated directly on the right atrial side of the central fibrous body in the muscular portion of the AV septum, just superior and anterior to the ostium 30 of the coronary sinus 30. Measuring approximately 1.0 mm×3.0 mm×6.0 mm, the node is flat and oval. The AV node 34 is located at the apex of the triangle of Koch 38, which is formed by the tricuspid annulus 22, the ostium 30 of the coronary sinus, and the tendon of Todaro 32. The AV node 34 continues on to the bundle of His 36, typically via a course inferior to the commissure 28 between the septal 24a and anterior 24b leaflets of the tricuspid valve; however, the precise course of the bundle of His 36 in the vicinity of the tricuspid valve may vary. Moreover, the location of the bundle of His 36 may not be readily apparent from a resected view of the right atrium because it lies beneath the annulus tissue.

The triangle of Koch 38 and tendon of Todaro 32 provide anatomic landmarks during tricuspid valve repair procedures. A major factor to consider during surgery is the proximity of the conduction system (AV node 34 and bundle of His 36) to the septal leaflet 24a. Of course, surgeons must avoid placing sutures too close to or within the AV node 34. C-shaped rings are good choices for tricuspid valve repairs because they allow surgeons to position the break in the ring adjacent the AV node 34, thus avoiding the need for suturing at that location.

An example of a rigid C-shaped ring is the Carpentier-Edwards Classic® Tricuspid Annuloplasty Ring discussed above. The Classic® ring has a gap between free ends. The gap provides a discontinuity to avoid attachment over the AV node. The gap for the various sizes ranges between about 5-8 mm, or between about 19%-22% of the labeled size.

Despite numerous designs presently available or proposed in the past, there is a need for a prosthetic tricuspid ring that better repairs certain conditions of the tricuspid annulus, and in particular reduces excessive chordal tethering, which tends to pull the leaflets apart leading to regurgitation.

SUMMARY OF THE INVENTION

The present invention provides a tricuspid annuloplasty ring including a ring body generally arranged in a plane and about an axis along an inflow-outflow direction. In plan view, the ring body further has at least one inflection point between adjacent concave and convex segments, with the concave segments corresponding to at least one of the native leaflets. In particular, the ring body has one inflection point between each pair of adjacent concave and convex segments, and there are desirably at least two concave segments so that there are at least four inflection points.

In one embodiment, the ring body is discontinuous so as to define a first free end and a second free end separated across a gap. For instance, the ring may be configured to contact and support the interior of the tricuspid annulus, and define, in sequence, a first free end, a first septal segment, an anterior segment, a posterior segment, and a second septal segment. Each of the segments is generally concave or straight and separated from adjacent segments by convex corners. The tricuspid ring may have a relatively straight first septal segment, an inward bow in the anterior segment defining, an inward bow in the posterior segment, and an inward bow in the second septal segment. Desirably, the inward bows extend inward by different distances. For example, the inward bow in the anterior segment may be greater than the inward bow in the posterior segment which is greater than the inward bow in the second septal segment.

In another form, the annuloplasty ring body is generally convex in plan view but has multiple concave segments around its periphery each defining an inward bow. Further, the ring body is preferably discontinuous so as to define a first free end and a second free end separated across a gap. The ring body may further includes one or more upward bows. In a preferred embodiment, the inward bows extend inward by different distances. In an absolute sense, the inward bows extend inward between 5%-25% of a corresponding nominal ring size.

Preferably, a tricuspid annuloplasty ring, has a ring body peripherally arranged about an axis and being discontinuous so as to define two free ends at a break in continuity around the ring body. A plan view of the ring body along the axis defines, in sequence, a first free end, a first septal segment, an anterior segment adapted to attach to the tricuspid annulus adjacent the anterior leaflet, a posterior segment adapted to attach to the tricuspid annulus adjacent the posterior leaflet, a second septal segment adapted to attach to the tricuspid annulus adjacent the septal leaflet, and a second free end, wherein one or more of the first septal segment, anterior segment, posterior segment, and second septal segment is at least partly concave defining an inward bow. Desirably there are two inward bows that extend inward by different distances. In one configuration, the inward bow in the anterior segment is greater than the inward bow in the posterior segment which is greater than the inward bow in the second septal segment. For instance, the inward bow in the anterior segment is between 15%-25% of a corresponding nominal ring size, P is between 10%-20% of a corresponding nominal ring size, and S is between 5%-15% of a corresponding nominal ring size. In a preferred embodiment, the concave segments define inward bows that are between 5%-25% of a corresponding nominal ring size.

A further understanding of the nature and advantages of the invention will become apparent by reference to the remaining portions of the specification and drawings.

BRIEF DESCRIPTION OF THE DRAWINGS

Features and advantages of the present invention will become appreciated as the same become better understood with reference to the specification, claims, and appended drawings wherein:

DETAILED DESCRIPTION OF THE PREFERRED EMBODIMENTS

The present invention provides an improved tricuspid annuloplasty ring shaped to repair certain conditions of the tricuspid annulus, through certain features might also be applicable and beneficial to rings for other of the heart's annuluses. It should be understood that annuloplasty rings in general are configured to contact and support the interior of one of the annuluses of the heart, as contrasted with sinus shaping devices or external cardiac belts or harnesses, for example.

The term "axis" in reference to the illustrated ring, and other non-circular or non-planar rings, refers to a line generally perpendicular to the ring that passes through the area centroid of the ring when viewed in plan view. "Axial" or the direction of the "axis" can also be viewed as being parallel to the direction of blood flow within the valve orifice and thus within the ring when implanted therein. Stated another way, the implanted tricuspid ring orients about a central flow axis aligned along an average direction of blood flow through the tricuspid annulus. Although the rings of the present invention may be 3-dimensional, they are typically planar and lie perpendicular to the flow axis.

Figure 7A:
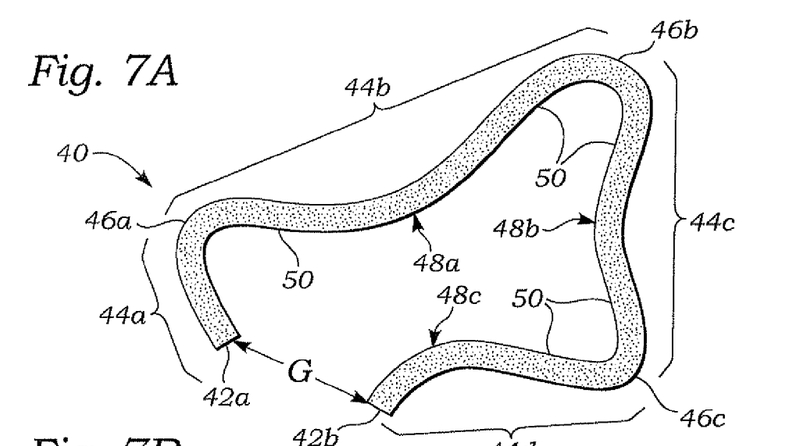
FIGS. 7A and 7B are plan and septal elevational views, respectively, of a tricuspid annuloplasty ring of the present invention.
Figure 7B:
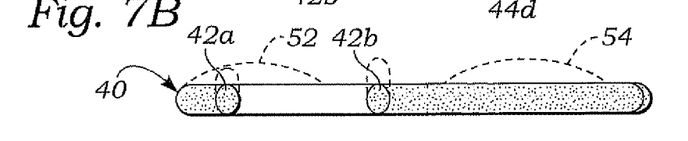

An exemplary tricuspid annuloplasty ring 40 is seen in FIGS. 7A and 7B. Although not shown, the ring 40 desirably has an inner core or ring body covered by a layer of silicone and then fabric. The ring body is not shown in the figures but it will be understood that it essentially defines the particular ring shape illustrated and described, as the suture-permeable outer layers (e.g., of silicone and fabric) typically conform closely therearound. Ribs or bulges in the suture-permeable outer layers may be provided, though they are not considered central to the present invention.

The inner core or ring body extends substantially around the entire periphery of the ring 40 and is a relatively or semi-rigid material such as stainless steel, titanium, Elgiloy (an alloy primarily including Ni, Co, and Cr), Nitinol, and even certain polymers. The term "relatively rigid" or "semi-rigid" refers to the ability of the core to support the annulus without substantial deformation, and implies a minimum elastic strength that enables the ring to maintain its original shape after implant even though it may flex somewhat. Indeed, the ring desirably possesses some small flexibility around its periphery. To further elaborate, the core would not be made of silicone, which easily deforms to the shape of the annulus and therefore will not necessarily maintain its original shape upon implant.

In one exemplary construction, the ring 40 includes a core made of a plurality of concentric peripheral bands. Such a concentric band construction is disclosed in U.S. Pat. No. 5,104,407 to Lam, et al. Another possible construction of the ring core is solid titanium (or suitable alternative) extending from the first free end 42a to the second free end 42b. Areas of increased flexibility or discrete hinge points may be formed by reducing the cross-sectional shape of the core at those locations. For example, to obtain greater up and down flexibility, the axial height of the core is reduced at a point or along a region. A particularly desirable result of any partially flexible core is ring flexibility "out of the plane" to allow the ring to accommodate different patient geometries, while maintaining ring stiffness in the "plane." In this sense, the "plane" is the nominal plane in which the majority of the annulus/ring resides. One of skill in the art will understand that any of the embodiments described herein, and combinations thereof, may be created by shaping a solid material core.

A suture-permeable interface typically provided around the core facilitates implant at the native annulus. The interface may be elastomeric, such as silicone, and provides bulk to the ring for ease of handling and implant, and permits passage of sutures though not significantly adding to the anchoring function of the outer fabric covering. The fabric covering may be any biocompatible material such as Dacron® (polyethylene terephalate). The elastomeric interface and fabric covering project slightly outwards along the outside of the ring 40 to provide a platform through which to pass sutures. An alternative interface is simply wrapped, bunched or rolled fabric, with no silicone.

As seen in inflow plan view along the axis in FIG. 7A, the ring 40 extends in a clockwise direction from a first free end 42a to a second free end 42b, the free ends defining a discontinuity in the ring across a gap G. The periphery of the ring 40 describes an overall convex shape that is sized to surround the native tricuspid leaflets. The term "overall convex" means that the ring 40 circumscribes a periphery and the aggregate of the various curves of the ring is convex so that the free ends 42a, 42b generally converge.

Rings for sizes 26 mm through 36 mm in 2 mm increments have outside diameters (OD) between 31.2-41.2 mm, and inside diameters (ID) between 24.3-34.3 mm. These diameters are taken along the "diametric" line spanning the greatest length across the ring because that is the conventional sizing parameter. The gap G for the various sizes ranges between about 5-8 mm, or between about 19%-22% of the labeled size.

Still with reference to FIG. 7A, the ring 40 defines, in sequence, the first free end 42a, a first septal segment 44a, an anterior segment 44b, a posterior segment 44c, and a second septal segment 44d. The segments 44a-44d are generally concave (inwardly curved) or at least not convex, and are separated by convex (outwardly curved) corners 46a, 46b, 46c. Desirably, the first septal segment 44a is relatively straight, the anterior segment 44b defines an inward bow 48a, the posterior segment 44c defines an inward bow 48b, and the second septal segment 44d also defines an inward bow 48c.

Inflection points 50 exist at five locations between the three corners 46a, 46b, 46c and the concave portions of each of the segments 44b, 44c, 44d. Inflection points are defined where the ring body changes from being convex to concave, or vice versa.

As seen in FIG. 7B, the exemplary ring 40 is desirably planar, but may also include one or more upward bows, such as a bow 52 seen in phantom in the first septal segment 44a and anterior segment 44b, and another upward bow 54 seen in phantom in the second septal segment 44d. The "aortic" bow 52 may accommodate a similar contour of the tricuspid annulus due to the external presence of the aorta and if provided may extend from near the first free end 56a along first septal segment 44a to a location that corresponds to the end of the aortic part of the anterior leaflet. Prior tricuspid rings are substantially planar, and if at all rigid they necessarily deform the annulus to some extent at this location. The aortic bow 52 helps reduce stress upon implant and concurrently reduces the chance of dehiscence, or the attaching sutures pulling out of the annulus. The axial height of the aortic bow 52 above the nominal top surface of the ring 40, is desirably between about 3-9 mm, preferably about 6 mm. The "septal" bow 54 conforms to the slight bulging of the septal leaflet attachment in this area. The axial height of the septal bow 54 above the nominal top surface of the ring 40, is desirably between about 2 to 4 mm. These two bows 52, 54 provide somewhat of a "saddle shape" to the ring body 40. In addition, the free ends 42a, 42b may also be upturned, as seen in phantom in FIG. 7B.

Figure 8:
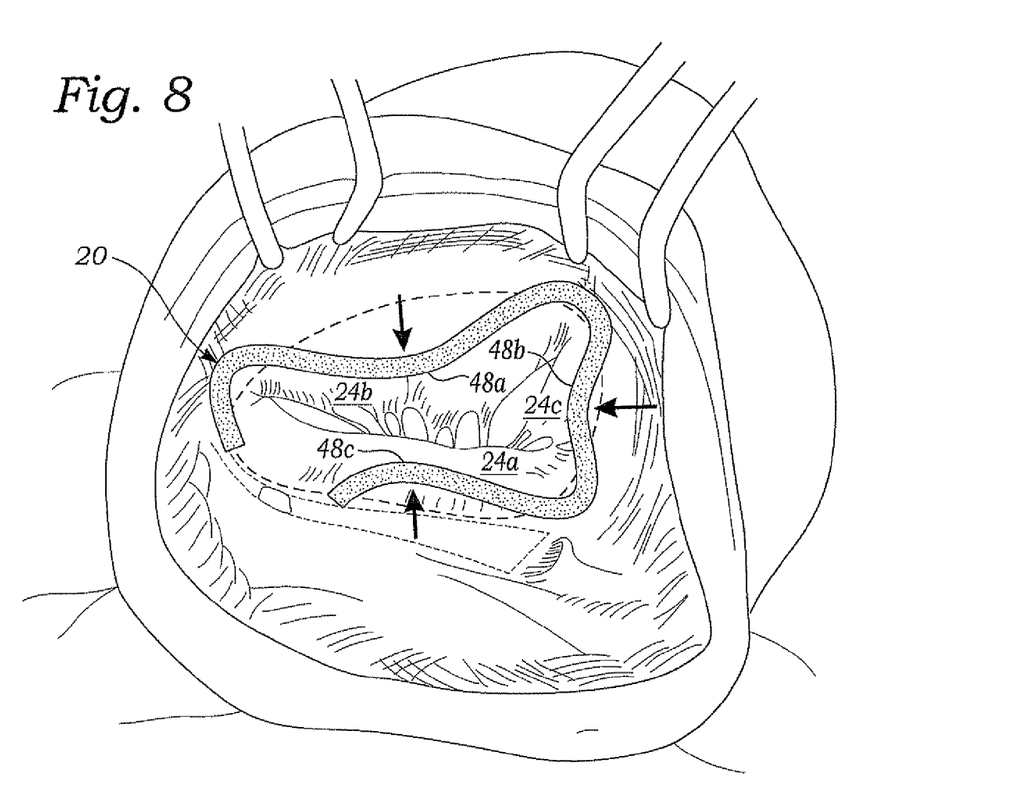
FIG. 8 is a plan view of the native tricuspid valve and surrounding anatomy from the inflow side with the annuloplasty ring of FIGS. 7A-7B implanted.

As seen in FIG. 8, the ring implants such that the segments 44b, 44c, 44d and corresponding to inward bows 48a, 48b, 48c register with the anterior leaflet 24b, posterior leaflet 24c, and septal leaflet 24a, respectively. That is, the anterior segment 44b registers with the anterior leaflet 24b, the posterior segment 44c registers with the posterior leaflet 24c, and the second septal segment 44d registers with the septal leaflet 24a. Likewise, the convex corners 46a, 46b, 46c correspond, respectively, with the antero septal commissure, posterior commissure, and postero septal commissure, as labeled in FIG. 5. The length and curvature of the second septal segment 44d is such that it traverses around the AV node 34 and the second free end 42b may be anchored adjacent thereto at the tricuspid annulus 22.

Figure 9:
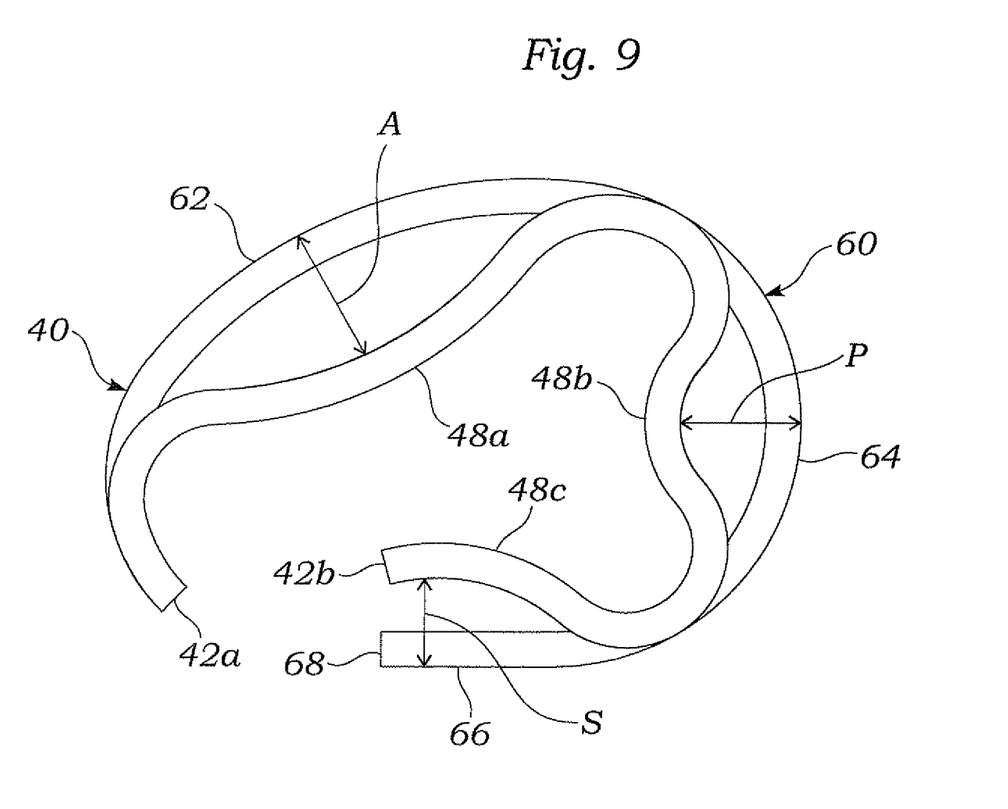
FIG. 9 is a plan view of a tricuspid annuloplasty ring of the present invention superimposed over a conventional tricuspid ring.

FIG. 9 is a plan view of a tricuspid annuloplasty ring 40 of the present invention superimposed over a conventional tricuspid ring 60. As described above, the tricuspid ring 40 has two free ends 42a, 42b separated across a gap and generally converge toward one another. The overall shape of the ring 40 is convex and sized to surround the native tricuspid leaflets, with labeled sizes preferably from 26 mm through 36 mm in 2 mm increments. The ring 40 in FIG. 9 is slightly modified from the earlier illustrations, having a more rounded or smoothed appearance. For example, a majority of each convex or concave arcuate portions of the ring 40, such as the inward bows 48a, 48b, 48c, describe a partial circular arc as opposed to having gradually changing radii.

The conventional tricuspid ring 60 shown below the ring 40 of the present invention comprises an anterior segment 62, a posterior segment 64, and a septal segment 66, as seen moving clockwise from a first free end (not shown) to a second free end 68. Each segment 62, 64, 66 is convex (outwardly curved) or at least not concave, and there are no points of inflection. The anterior segment 62 is the longest, spanning approximately one-half of the circumference of the ring 40. The posterior segment 64 is the next longest, spanning about one-third of the circumference of the ring 40. And the septal segment 66 is the shortest and is typically linear except for a small curve at the junction with the posterior segment 64 and depending on where the dividing line is drawn.

The gap between the two free ends 42a, 42b of the ring 40 approximately equals the gap between the two free ends of the conventional ring 60. The second free end 42b of the ring 40 terminates radially inward from the second free end 68 of the conventional ring 60. Each of the inward bows 48a, 48b, 48c extends inward by distances labeled A, P, and S, respectively, from the corresponding segment of the conventional ring 60. That is, the inward bow 48a extends inward a distance A from the anterior segment 62, the inward bow 48b extends inward a distance P from the posterior segment 64, and the inward bow 48c extends inward a distance S from the septal segment 66. The dimensions A, P, and S are measured at the point of largest separation between the inward bows 48a, 48b, 48c and the corresponding segments, typically the midpoint of each inward bow. However, it is conceivable that the inward bows 48a, 48b, 48c are asymmetrically curved so that the radially innermost point of any one of the inward bows is offset from its midpoint thereof. In a preferred embodiment, the dimensions A, P, and S are sized relative to the nominal ring size (e.g., between 26 and 40 mm), and desirably A>P>S. In a particularly preferred embodiment, the inward bows are between 5%-25% of the nominal ring size. For instance, A is between 15%-25% of the nominal ring size, P is between 10%-20% of the nominal ring size, and S is between 5%-15% of the nominal ring size. So, looking at a ring having a nominal size of 36 mm, and taking the maximum of the aforementioned ranges, A =9 mm, P=7.2 mm, and S=5.4 mm.

The implant technique may be via a traditional parachute suture array, where the sutures are pre-implanted around the annulus and then ex vivo through the outside edge of the ring 40, whereupon the surgeon slides the ring down the array of sutures into place, thus conforming the annulus to the ring. The mid-portion of each of the segments 44b, 44c, 44d bows inward, which accordingly pulls the native tricuspid annulus inward, as indicated by the bold inward directional arrows. This affords more slack to each of the leaflets, which in turn helps reduce excessive chordal tethering. That is, some tricuspid pathologies such as leaflet thickening increase tension in the chordai, which in turn leads to tethering and regurgitation. Moving the leaflet midpoints inward by implanting the exemplary tricuspid ring 40 disclosed herein mitigates this problem.

The beneficial aspect of the inward bows 48a, 48b, 48c is desirably realized with one for each leaflet. However, the inward bows may be provided for just one or two of the leaflets, depending on the need.

The extent of the inward bows 48a, 48b, 48c is also variable, with a radially inward dimension of between about 2-10 mm being preferred. Likewise, the preferred shape is gently contoured curves, though other shapes are conceivable.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A prosthetic tricuspid annuloplasty ring, comprising:
   a ring body generally arranged about a flow axis along an inflow-outflow direction, the ring body being overall convex and asymmetric in plan view looking along the axis and having at least three inflection points around the ring periphery in plan view and extending around the periphery in a single elongated member without branches and lying generally perpendicular to the axis, wherein the ring is configured to contact and support the interior of the tricuspid annulus, and defines in plan view, in sequence, a first free end, a first septal segment, an anterior segment adapted to attach to the tricuspid annulus adjacent the anterior leaflet and spanning an equivalent peripheral distance, a posterior segment adapted to attach to the tricuspid annulus adjacent the posterior leaflet and spanning an equivalent peripheral distance, and a second septal segment adapted to attach to the tricuspid annulus adjacent the septal leaflet, wherein each of the anterior, posterior and second septal segments is generally concave inward, and a second free end separated across a gap from the first free end such that the ring is discontinuous, and wherein two of the inflection points are in the anterior segment.

2. The annuloplasty ring of claim 1, wherein the first septal segment is relatively straight.

3. The annuloplasty ring of claim 1, wherein the inward bows extend inward by different distances.

4. The annuloplasty ring of claim 3, wherein the inward bow in the anterior segment is greater than the inward bow in the posterior segment which is greater than the inward bow in the second septal segment.

5. The annuloplasty ring of claim 2, wherein the inward bow in the anterior segment is between 15%-25% of a corresponding nominal ring size, P is between 10%-20% of a corresponding nominal ring size, and S is between 5%-15% of a corresponding nominal ring size.

6. The annuloplasty ring of claim 2, wherein the inward bows are between 5%-25% of a corresponding nominal ring size.

7. The annuloplasty ring of claim 1, wherein the ring body further includes one or more upward bows.

8. The annuloplasty ring of claim 7, wherein an upward bow exists in the first septal segment and anterior segment, and another upward bow exists in the second septal segment.

9. A prosthetic tricuspid annuloplasty ring, comprising:
a ring body generally arranged about a flow axis along an inflow-outflow direction, the ring body being overall convex and asymmetric in plan view looking along the axis but having multiple concave segments defining inward bows around the ring periphery in plan view and extending around the periphery in a single elongated member without branches and lying generally perpendicular to the axis, wherein at least one of the concave segments is between adjacent convex corners, wherein the ring is configured to contact and support the interior of the tricuspid annulus, and defines in plan view, in sequence, a first free end, a first septal segment, an anterior segment adapted to attach to the tricuspid annulus adjacent the anterior leaflet and spanning an equivalent peripheral distance, a posterior segment adapted to attach to the tricuspid annulus adjacent the posterior leaflet and spanning an equivalent peripheral distance, and a second septal segment adapted to attach to the tricuspid annulus adjacent the septal leaflet, and a second free end separated across a gap from the first free end such that the ring is discontinuous, and wherein there is one inward bow in each of the anterior segment and posterior segment.

10. The annuloplasty ring of claim 9, wherein each of the segments is generally concave or straight and separated from adjacent segments by convex corners.

11. The annuloplasty ring of claim 9, wherein the first septal segment is relatively straight and the second septal segment defines an inward bow.

12. The annuloplasty ring of claim 11, wherein the inward bow in the anterior segment is greater than the inward bow in the posterior segment which is greater than the inward bow in the second septal segment.

13. The annuloplasty ring of claim 11, wherein the inward bow in the anterior segment is between 15%-25% of a corresponding nominal ring size, P is between 10%-20% of a corresponding nominal ring size, and S is between 5%-15% of a corresponding nominal ring size.

14. The annuloplasty ring of claim 9, wherein the inward bows extend inward by different distances.

15. The annuloplasty ring of claim 9, wherein the inward bows are between 5%-25% of a corresponding nominal ring size.

16. The annuloplasty ring of claim 9, wherein the ring body further includes one or more upward bows.

17. A prosthetic tricuspid annuloplasty ring, comprising:
a ring body peripherally arranged about a flow axis in a single elongated member without branches and lying generally perpendicular to the axis and being discontinuous so as to define two free ends at a break in continuity around the ring body, wherein a plan view of the ring body along the axis is asymmetric and defines, in sequence:
a first free end;
a first septal segment adapted to attach to the tricuspid annulus adjacent a portion of the septal leaflet;
an anterior segment adapted to attach to the tricuspid annulus adjacent the anterior leaflet and defining an inward bow segment adapted to attach to the tricuspid annulus adjacent the anterior leaflet and spanning an equivalent peripheral distance;
a posterior segment adapted to attach to the tricuspid annulus adjacent the posterior leaflet and defining an inward bow adapted to attach to the tricuspid annulus adjacent the posterior leaflet and spanning an equivalent peripheral distance;
a second septal segment adapted to attach to the tricuspid annulus adjacent a portion of the septal leaflet adapted to attach to the tricuspid annulus adjacent the septal leaflet; and
a second free end.

18. The annuloplasty ring of claim 17, wherein at least one of the first septal segment and second septal segment are at least partly concave defining an inward bow that extends inward by a different distance than either the anterior bow or the posterior bow.

19. The annuloplasty ring of claim 18, wherein the anterior segment, posterior segment, and second septal segment include inward bows wherein the inward bow in the anterior segment is greater than the inward bow in the posterior segment which is greater than the inward bow in the second septal segment.

20. The annuloplasty ring of claim 19, wherein the inward bow in the anterior segment is between 15%-25% of a corresponding nominal ring size, P is between 10%-20% of a corresponding nominal ring size, and S is between 5%-15% of a corresponding nominal ring size.

21. The annuloplasty ring of claim 17, wherein the inward bow extends inward between 5%-25% of a corresponding nominal ring size.

* * * * *